(12) United States Patent
Nelson et al.

(10) Patent No.: US 9,874,559 B2
(45) Date of Patent: Jan. 23, 2018

(54) CAPACITIVE PUMPING AND FLOW CONTROL

(75) Inventors: James Curtis Nelson, Raleigh, NC (US); David Ure, Wellesley, MA (US)

(73) Assignee: INANOVATE, INC., Research Triangle Park, NC (US)

( * ) Notice: Subject to any disclaimer, the term of this patent is extended or adjusted under 35 U.S.C. 154(b) by 147 days.

(21) Appl. No.: 13/989,642

(22) PCT Filed: Mar. 29, 2011

(86) PCT No.: PCT/US2011/030240
§ 371 (c)(1),
(2), (4) Date: May 24, 2013

(87) PCT Pub. No.: WO2012/071070
PCT Pub. Date: May 31, 2012

(65) Prior Publication Data
US 2013/0236335 A1    Sep. 12, 2013

Related U.S. Application Data

(63) Continuation-in-part of application No. 12/956,117, filed on Nov. 30, 2010, now Pat. No. 8,975,087, and
(Continued)

(51) Int. Cl.
*F04B 43/00* (2006.01)
*B01L 3/00* (2006.01)
(Continued)

(52) U.S. Cl.
CPC ........ *G01N 33/557* (2013.01); *B01L 3/50273* (2013.01); *F04B 43/0009* (2013.01);
(Continued)

(58) Field of Classification Search
CPC ........... B01L 3/502738; B01L 3/50273; B01L 2400/0487; B01L 2200/10;
(Continued)

(56) References Cited

U.S. PATENT DOCUMENTS 4,012,178 A    3/1977    Puckett
5,074,765 A    12/1991   Pekar
(Continued)

FOREIGN PATENT DOCUMENTS

EP    2273404 A1    1/2011
WO    9310455 A1    5/1993
(Continued)

OTHER PUBLICATIONS

Patent Cooperation Treaty, Notification of Trasmittal of the International Search Report and the Written Opinion on the International Searching Authority of PCT/US2014/24396 dated Jul. 8, 2014, 34 pages.
(Continued)

*Primary Examiner* — Erik B Crawford
(74) *Attorney, Agent, or Firm* — Hoffman Warnick LLC

(57) ABSTRACT

Embodiments of the invention relate generally to devices and methods for pumping and controlling the flow of a fluid. More particularly, embodiments of the invention relate to capacitive pumping and flow control devices and methods. In one embodiment, the invention provides a pump system having an inlet valve, an outlet valve, and a chamber between and in communication with each of the inlet valve and the outlet valve, the chamber having at least one elastic surface, wherein the chamber will dilate in response to a fluid exerting a pressure on the elastic surface, contain a quantity of the fluid when so dilated, and discharge the quantity of the fluid through the opened outlet valve.

14 Claims, 8 Drawing Sheets

Related U.S. Application Data a continuation-in-part of application No. PCT/US2010/058112, filed on Nov. 24, 2010.

(51) Int. Cl.

| | | |
|---|---|---|
| *G01N 33/557* | (2006.01) | |
| *G01N 33/53* | (2006.01) | |
| *F04B 43/02* | (2006.01) | |
| *F04B 43/04* | (2006.01) | |
| *F04B 43/06* | (2006.01) | |

(52) U.S. Cl.
CPC .............. *F04B 43/02* (2013.01); *F04B 43/04* (2013.01); *F04B 43/06* (2013.01); *G01N 33/5302* (2013.01); *B01L 2300/0816* (2013.01); *B01L 2300/123* (2013.01)

(58) Field of Classification Search
CPC ..... B01L 2300/0861; B01L 2300/0887; B01L 2400/0481; B01L 3/502715; B01L 2200/0621; B01L 3/5027; B01L 2300/0867; B01L 2300/123; B01L 3/502746; B01L 2300/0864; B01L 3/5025; B01L 2200/026; B01L 2200/0605; B01L 2200/0647; B01L 2300/14; B01L 2400/0478; B01L 2400/06; B01L 2400/0633; B01L 3/502; A61M 1/1037; A61M 5/14593; A61M 1/1062; A61M 2205/123; A61M 2205/128; A61M 39/22; A61M 5/16809; A61M 1/106; A61M 1/3621; A61M 1/1649; G01N 33/5302; G01N 35/1095
USPC .......... 435/287.9, 288.5, 288.6, 286.5, 287.3; 417/395, 480, 390, 478; 422/504, 68.1, 422/81, 82; 92/96
See application file for complete search history.

(56) References Cited

U.S. PATENT DOCUMENTS

| | | | |
|---|---|---|---|
| 5,089,387 A | 2/1992 | Tsay et al. | |
| 5,372,487 A | 12/1994 | Pekar | |
| 6,382,923 B1 | 5/2002 | Gray | |
| 6,908,594 B1 | 6/2005 | Schaevitz et al. | |
| 2004/0191818 A1 | 9/2004 | O'Toole et al. | |
| 2005/0033520 A1 | 2/2005 | Dai et al. | |
| 2006/0263907 A1 | 11/2006 | Zweig | |
| 2007/0074972 A1 | 4/2007 | Nassef et al. | |
| 2007/0074973 A1 | 4/2007 | Nassef et al. | |
| 2008/0199482 A1 | 8/2008 | Dijkstra et al. | |
| 2009/0099498 A1* | 4/2009 | Demers et al. | 604/6.09 |
| 2009/0192410 A1 | 7/2009 | Freeman et al. | |
| 2009/0305332 A1 | 12/2009 | Haendler et al. | |
| 2010/0068822 A1* | 3/2010 | Heydenhauss et al. | 436/172 |
| 2010/0298684 A1 | 11/2010 | Leach et al. | |
| 2011/0020918 A1 | 1/2011 | Nassef et al. | |
| 2011/0092389 A1 | 4/2011 | Dickinson et al. | |
| 2011/0212453 A1* | 9/2011 | Agarwal | B01L 3/502715 435/6.12 |
| 2011/0257732 A1 | 10/2011 | McClain et al. | |
| 2011/0262896 A1 | 10/2011 | Blecka et al. | |
| 2012/0282684 A1 | 11/2012 | Fritchie et al. | |

FOREIGN PATENT DOCUMENTS

| | | |
|---|---|---|
| WO | 2006101550 A1 | 9/2006 |
| WO | 2012007783 A1 | 1/2012 |
| WO | 2012037369 A1 | 3/2012 |

OTHER PUBLICATIONS

Burry, "Controls for Immunocytochemistry: An Update," 2011, pp. 6-12, Journal of Histochemistry & Cytochemistry.
SIGMA Life Science, "qPCR Technical Guide," retrieved May 23, 2014 at http://www.sigmaaldrich.com/life-science/molecular-biology/pcr/quantitative-per/qpcr-technicalguide.html, pp. 1-40.
Patent Cooperation Treaty, PCT Notification of Transmittal of International Search Report and the Written Opinion of the International Searching Authority, or the Declaration dated Jul. 22, 2011 for PCT/US2010/058112, 14 pages.
Dai et al., "Use of Hybridization Kinetics for Differentiating Specific From Non-Specific Binding to Oligonucleotide Microarrays," dated May 2002, pp. 1-8, Nucleic Acids Research, vol. 30, No. 16.
Furusawa et al., "Model-Based Analysis of Non-Specific Binding for Background Correction of High-Density Oligonucleotide Microarrays," Oct. 2008, pp. 36-41, Bioinformatics, vol. 25, No. 1.
Patent Cooperation Treaty, PCT Notification of Transmittal of International Preliminary Report on Patentability and the Written Opinion of the International Searching Authority dated Jun. 6, 2013 for PCT/US2010/058112, 9 pages.
Wang et al., "Pre-binding dynamic range and sensitivity enhancement for immuno-sensors using nanofluidic preconcentrator," 2008, pp. 392-394, Lab Chip.
Peytavi et al., "Microfluidic Device for Rapid Automated Microarry Hybridization," 2005, pp. 1836-1844, Clinical Chemistry 51:10.
Counts, Office Action Communication for U.S. Appl. No. 12/956,117 dated Jul. 18, 2013, 13 pages.
Patent Cooperation Treaty, Notification of Transmittal of the International Search Report and the Written Opinion of the International Searching Authority for PCT/US2011/030240 dated Sep. 27, 2011, 14 pages.
Counts, Office Action Communication for U.S. Appl. No. 12/956,117 dated Apr. 17, 2014, 16 pages.
Counts, Notice of Allowance and Fees(s) Due for U.S. Appl. No. 12/956,117 dated Nov. 7, 2014, 12 pages.

* cited by examiner

CAPACITIVE PUMPING AND FLOW CONTROL

CROSS-REFERENCE TO RELATED APPLICATIONS

This application is related in some aspects to and claims the benefit as a continuation-in-part of each of co-pending International Patent Application No. PCT/US10/58112, filed 24 Nov. 2010 and co-pending U.S. patent application Ser. No. 12/956,117, filed 30 Nov. 2010, each of which is hereby incorporated herein.

BACKGROUND

Pumping devices and systems for moving quantities of fluids are known and employed in a great many contexts. Most pumping devices and systems may be categorized as positive displacement or dynamic. Positive displacement pumps and systems, in turn, may be categorized as reciprocating or rotary. Regardless of their classification, known pumping devices and systems suffer from a number of deficiencies that render them either inefficient or inoperable in some contexts.

Syringe pumps, for example, require operation of a piston, moved by a gear or similar mechanism, rendering the pumps subject to mechanical failure. In addition, altering the volume pumped or other parameters requires manipulation of the mechanism. Peristaltic pumps similarly rely on an external mechanism to provide the force necessary to move a fluid.

An electroosmotic pump, considered a dynamic pump, does not move fluids by mechanically-generated forces and therefore does not suffer from some of the deficiencies associated with such external mechanisms. However, electroosmotic pumps require the application of an electric field to the fluid, imparting significant limitations and inefficiencies to their operation. Electroosmotic pumps also tend to result in very high pressures (up to about 5,000 PSI) and/or flow rates, rendering them unsuitable for some applications.

Pressure pumps similarly do not necessarily rely on a mechanical force during their operation. Instead, pressure pumps rely on a reservoir of fluid stored under pressure and the operation of a valve or similar device for controlling fluid flow from the reservoir. Some mechanical force is generally employed, however, in pressurizing fluid within the reservoir. In addition, the pressure and/or flow rate achievable using a pressure pump is dependent upon the pressure within the reservoir, which generally decreases as fluid is drained from it.

BRIEF DESCRIPTION

Embodiments of the invention relate generally to systems, devices, and methods for pumping and/or controlling the flow of a fluid. More particularly, embodiments of the invention relate to capacitive pumping and flow control.

In one embodiment, the invention provides a pump system comprising: an inlet valve; an outlet valve; and a chamber between and in communication with each of the inlet valve and the outlet valve, the chamber having at least one elastic surface, wherein the chamber is adapted to: dilate in response to a fluid exerting a pressure on the at least one elastic surface; contain a quantity of the fluid when so dilated; and discharge the quantity of the fluid through the opened outlet valve.

In another embodiment, the invention provides a pump system comprising: an inlet valve; an outlet valve; and a chamber between and in communication with each of the inlet valve and the outlet valve, the chamber being adapted to: receive, through the open inlet valve, a quantity of a compressible fluid at a first pressure; hold the quantity of the compressible fluid at a second pressure greater than the first pressure against the closed inlet valve and the closed outlet valve; and discharge the quantity of the compressible fluid through the open outlet valve.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements among the drawings.

DETAILED DESCRIPTION

Figure 1:
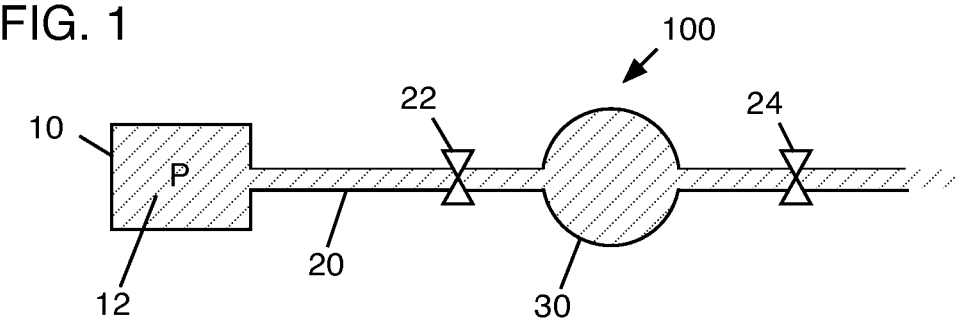
FIGS. 1-4 show schematic views of a pumping system according to an embodiment of the invention.

Embodiments of the invention have proven applicable to a wide range of contexts in which a fluid need be pumped and/or its flow controlled. Some embodiments have proven particularly useful in contexts in which a fluid must be passed through a device or system by incorporating a pumping/flow control mechanism of the invention directly into the device or system.

For example, FIGS. 1-4 show simple schematic views of the operation of a pumping system 100 according to an embodiment of the invention. As will be apparent from the description that follows, pumping system 100 may be used to pump a fluid and/or to control its flow. Pumping system 100 includes a reservoir 10 of fluid 12, an elastic or dilatable chamber 30, a channel 20, an inlet valve 22, and an outlet valve 24.

Reservoir 10 and channel 20 may include any material(s) suitable for holding and transporting, respectively, fluid 12. Inlet valve 22 and outlet valve 24, although described as valves merely for purposes of illustration, may be or include any number of devices or mechanisms suitable for alternately permitting and preventing passage of fluid 12. Such devices and mechanisms include, for example, a ball valve, a gate valve, an electronically-controlled valve (such as a pneumatic or hydraulic solenoid valve), or a clamping device, in the case that a channel to which the clamping device is connected and through which a fluid will pass, is sufficiently flexible or deformable.

Fluid 12 may include, for example, a liquid, a gas, a supercritical fluid, and mixtures and combinations thereof. Such fluids include, but are not limited to, water, aqueous solutions, organic solvents, organic solvent-based solutions, biological solutions, blood, serum, urine, saliva, sweat, fluidized particles, fluids containing suspended particles, methanol, air, nitrogen, helium, neon, oxygen, carbon monoxide, carbon dioxide, methane, fluorine, chlorine, ozone, and hydrogen.

Fluid 12 is stored within reservoir 10 at a static head pressure P. That is, fluid 12 need not be artificially pressurized, as required with other pumping systems. Chamber 30, as will be described in more detail below, comprises an elastic hollow member adapted to dilate in response to exertion of a pressure, i.e., head pressure P, on at least one of its surfaces. Accordingly, at least a portion of chamber 30 includes an elastic material capable of deformation in response to head pressure P. Suitable materials include, but are not limited to, silicones, polydimethylsiloxane (PDMS), neoprene, fluoroelastomers, fluoropolymers, natural rubber, latex, nitriles, chlorosulfonated polyethylene (CSPE) synthetic rubber (CSM), thermoplastic rubber (TPR), synthetic polyisoprene, polyurethanes, polyvinylchlorides (PVCs), polyurethanes, carbon, metals vinyls, or mixtures thereof.

In FIG. 1, both inlet valve 22 and outlet valve 24 are in their open positions. As such, fluid 12 passes through channel 20, inlet valve 22, chamber 30, and outlet valve 24.

Figure 2:
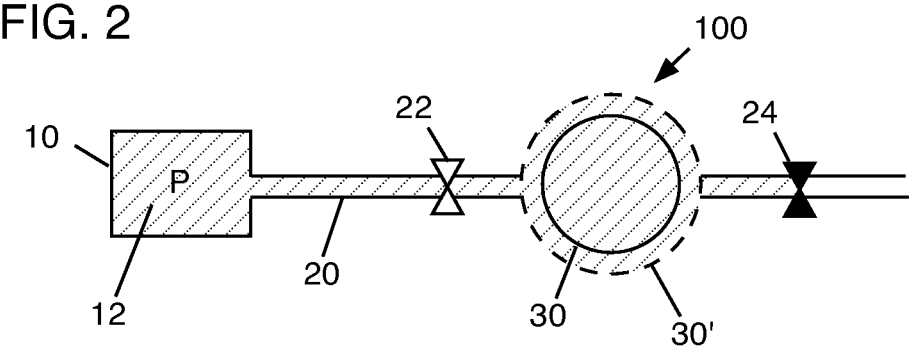

In FIG. 2, outlet valve 24 has been closed, causing fluid 12 to exert its head pressure P against chamber 30. As a result, chamber 30 dilates 30', increasing its volume. The extent to which chamber 30 will dilate depends, for example, on the material(s) of which it is composed, the thickness of such material(s), and head pressure P. Typical maximum dilation of chamber 30 will be between about 101% and about 200% of its undilated or zero-pressure volume. In some embodiments of the invention, chamber 30 is adapted to dilate in a substantially linear manner in response to each unit (e.g., pounds per square inch) increase in head pressure P, with a corresponding substantially linear increase in volume.

Merely for purposes of illustration and description, dilation 30' is shown to a substantially equal extent in all directions. It should be noted, however, that this is neither necessary nor essential. Just as the materials and thickness (es) of chamber 30 will affect the extent of dilation 30', so too will variations in materials and thicknesses of chamber 30. That is, chamber 30 may dilate substantially equally in three dimensions or may dilate more, less, or not at all in some directions.

Figure 3:
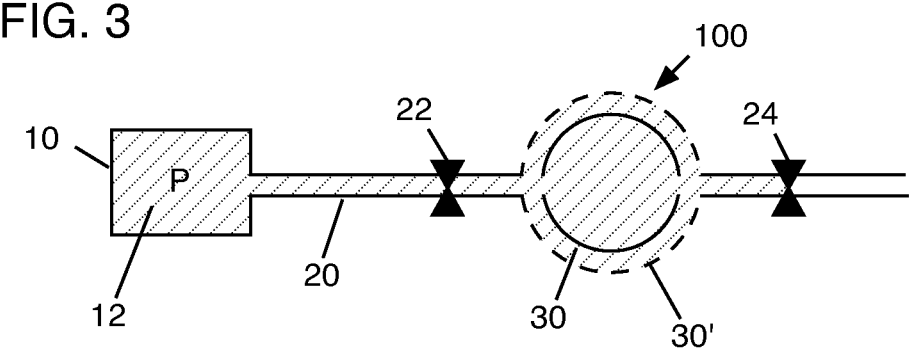

In FIG. 3, inlet valve 22 has also been closed, trapping a quantity of fluid 12 between inlet valve 22 and outlet valve 24. The maximum volume of the quantity of fluid 12 so trapped is determined, in part, by the extent of dilation 30'. However, volumes less than the maximum volume may be trapped by controlling the time during which outlet valve 24 is closed and inlet valve 22 is open, as in FIG. 2. That is, closing inlet valve 22, as shown in FIG. 3, before chamber 30 has dilated 30' to its maximum extent, will reduce the volume trapped and thus the volume pumped by pumping system 100.

Holding the trapped quantity of fluid 12, as in FIG. 3, for a period of time, may be useful in a number of contexts, such as where chamber 30 comprises or includes an assay chamber and/or a micro reactor. In such contexts, the trapped quantity of fluid 12 may be held for a period of time sufficient for an assay or reaction to be effective. Such embodiments and contexts will be described in greater detail below.

Figure 4:
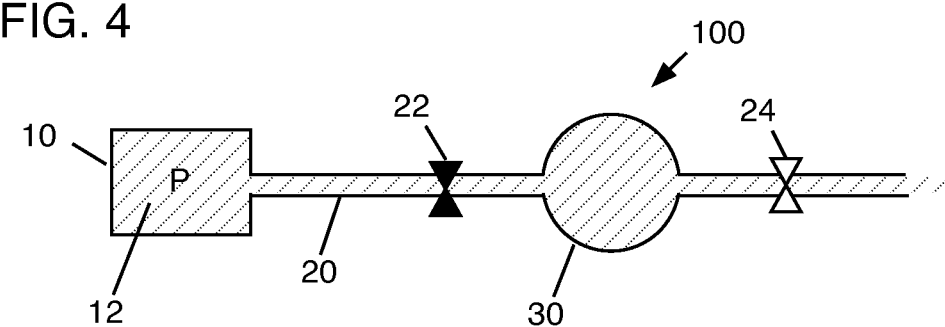

In FIG. 4, outlet valve 24 has been opened, thereby discharging the quantity of fluid 12 trapped in FIG. 3. Inlet valve 22 may then be opened, returning pumping system 100 to the state shown in FIG. 1, with flow through FIGS. 1-4 optionally being iterated. Such iteration may be useful, for example, in contexts in which chamber 30 comprises or includes a device through which fluid 12 passes, e.g., in which quantities of fluid 12 are to be repeatedly assayed in an assay chamber or catalyzed in a micro reactor.

In other contexts, such iteration may be useful in repeatedly delivering quantities of fluid 12 to some device, system, or reaction downstream of outlet valve 24. One context in which pumping system 100 may be particularly useful is in the delivery of a fluid within an animal body. For example, pumping system 100 may comprise an implantable system for pumping or circulating a body fluid, such as blood. In such a case, pumping system 100 may function as an artificial heart. In other cases, pumping system 100 may be used to deliver or circulate a pharmaceutical, therapeutic, or prophylactic composition within an animal, such as a human. In still other cases, pumping system 100 may be used to mix various components in which precise control of mixing conditions, proportions, etc. is desirable, such as the mixing of foods, perfumes, inks, pharmaceutical compositions, etc.

Iteratively operating pumping system 100 through the stages shown in FIGS. 1-4 may be used to pump substantially equal quantities of fluid 12 where inlet valve 22 is held open, as in FIG. 2, for substantially equal periods.

In other contexts, pumping system 100 may be used to pump different quantities of fluid 12 by holding inlet valve 22 open for differing periods. This may be particularly useful, for example, where other parameters within which pumping system 100 operates either necessarily remain substantially constant and/or are difficult to change. While known systems and devices would require manipulation of external devices, e.g., gears, pistons, etc. in order to alter the quantity of fluid 12 pumped, pumping system 100 permits doing so simply by varying the duration for which inlet valve 22 is held open.

In still other contexts, pumping system 100 may be operated to substantially compensate for a change in some other parameter within which pumping system 100 operates. For example, a decrease in head pressure P may result in a decrease in the rate of dilation 30' of chamber 30. In such a case, at a first head pressure P1, inlet valve 22 may have been held open for a first period that did not permit maximum dilation 30' of chamber 30. At a second head pressure P2 less than first head pressure P1, which would dilate chamber 30 more slowly, inlet valve 22 may be held open for a second period greater than the first period, permitting dilation 30' to an extent substantially equal to that under the first head pressure P1.

Similarly, whereas known systems and devices require significant alteration of external mechanisms to compensate for a change, for example, in the composition of fluid 12, pumping system 100 permits doing so simply by varying the duration for which inlet valve 22 is held open. Accordingly, pumping system 100 is operable to pump and/or control the flow of substantially equal quantities of fluid 12 as head pressure and/or other parameters vary.

Pumping system 100 permits both the pumping and/or flow control of very small (e.g., sub-microliter) volumes of fluid 12 and very rapid (e.g., less than one millisecond) cycling (i.e., flow through the states shown in FIGS. 1-4). This makes pumping system 100 very useful in micro-assay and micro-reaction contexts.

Figure 5:
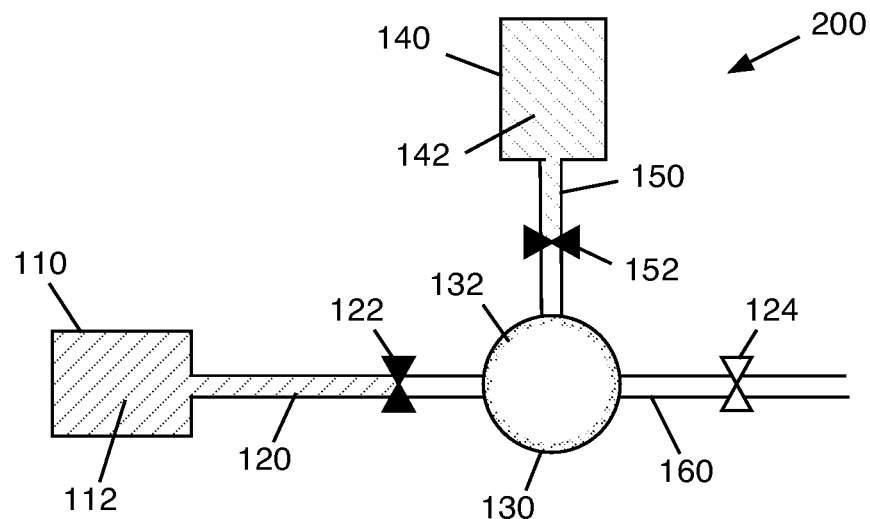
FIGS. 5-8 show schematic views of a micro reactor system according to an embodiment of the invention.

For example, FIGS. 5-8 show simple schematic views of a micro reactor system 200 according to an embodiment of the invention. In FIG. 5, it can be seen that micro reactor system 200 includes a first reservoir 110 containing a first fluid 112, a second reservoir 140 containing a second fluid 142, and a chamber 130 in communication with first reservoir 110 and second reservoir 140 via a first channel 120 and second channel 150, respectively. A first inlet valve 122 and second inlet valve 152 control flow of first fluid 112 and second fluid 142, respectively, into chamber 130. An outlet channel 160 and outlet valve 124 permit discharge of fluids from chamber 130.

Chamber 130 includes a reaction area 132, which may include, for example, an area of nano-particle catalysts capable of catalyzing a reaction between first fluid 112 and second fluid 142. The composition, particle size, etc. of such catalysts will vary, of course, depending on the compositions of first fluid 112 and second fluid 142 and the desired reaction therebetween. In other embodiments of the invention, the reaction area may be included on a rod or similar device capable of being inserted into chamber 130.

Figure 6:
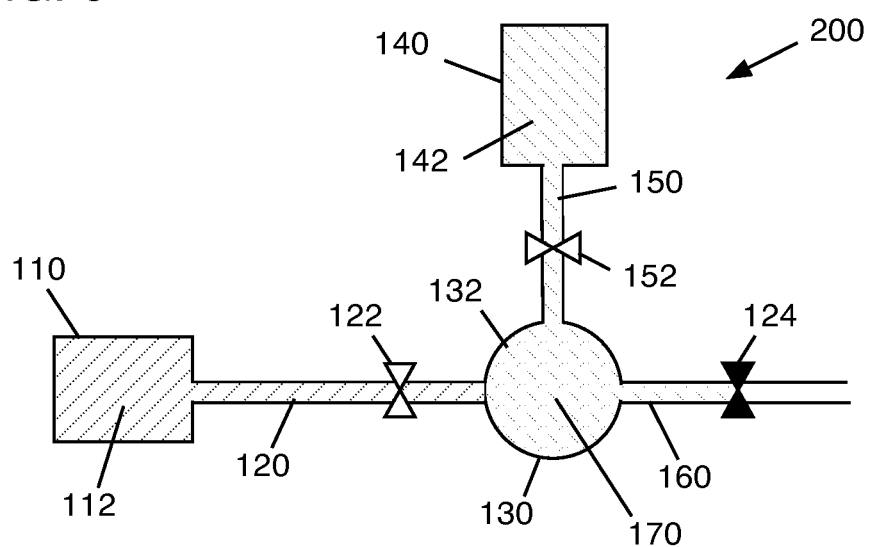

In FIG. 5, first inlet valve 122 and second inlet valve 152 are closed, such that first fluid 112 and second fluid 142, respectively, are prevented from entering chamber 130. In FIG. 6, both first inlet valve 122 and second inlet valve 152 have been opened, permitting flow of first fluid 112 and second fluid 142 into chamber 130, and outlet valve 124 has been closed. Upon combining within chamber 130 and contact with reaction area 32 (FIG. 5), first fluid 112 and second fluid 142 form a reacted fluid 170.

Figure 7:
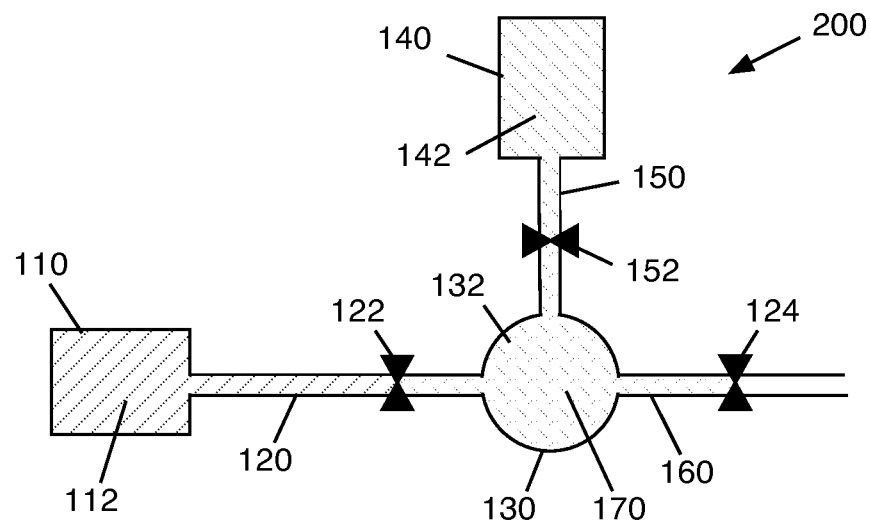
Figure 8:
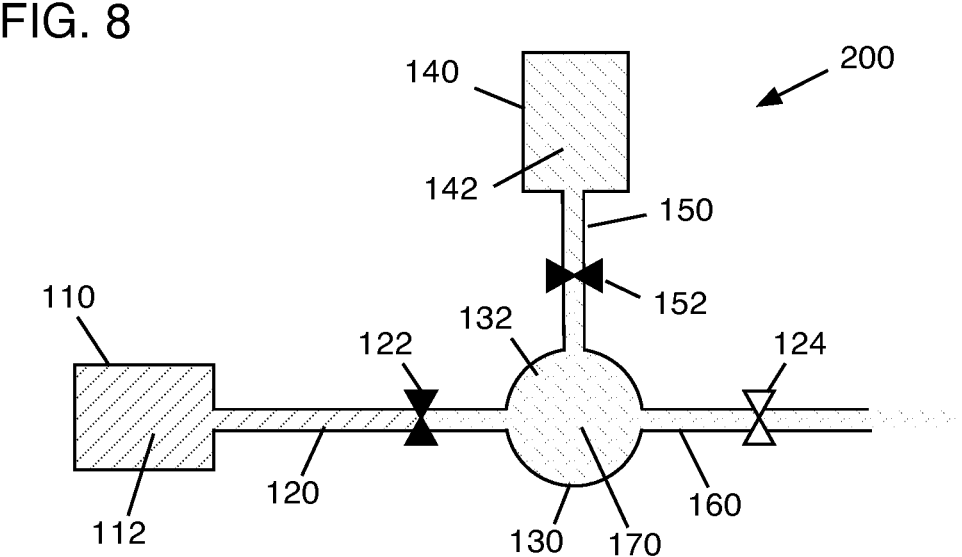

In FIG. 7, first inlet valve 122 and second inlet valve 152 have been closed. This may be done to permit a sufficient period of time to complete the reaction of first fluid 112 and second fluid 142. In FIG. 8, outlet valve 124 has been opened, permitting the discharging of reacted fluid 170.

While the description above includes the simultaneous or near-simultaneous opening of first inlet valve 122 and second inlet valve 152, this is neither necessary nor essential. For example, in some embodiments, the desired reaction of first fluid 112 and second fluid 142 may include an initial catalyzation of either fluid. In such a case, first inlet valve 122 may be opened first, permitting first fluid 112 to flow into chamber 130 and react with the catalyst(s) in reaction area 132. Second inlet valve 152 may then be opened, permitting flow of second fluid 142 into chamber to react with the already-catalyzed first fluid 112. Such differential opening of first inlet valve 122 and second inlet valve 152 may result in a different reacted fluid 170 than if the valves were opened together.

In some embodiments of the invention, chamber 130 may be capable of dilation, as in the embodiments shown in FIGS. 1-4, although this is neither necessary nor essential. In other embodiments of the invention, chamber 130 may include or be comprised of substantially rigid or inelastic materials.

For example, embodiments of the invention in which chamber 130 is substantially inelastic may be employed in reacting one or more compressible fluids, such as a gas. In such cases, chamber 130 may include materials such as, but not limited to, ethyl vinyl acetate, fluororesin (PFA), a nylon, a polyamide, a polyethylene, a cross-linked polyethylene, polypropylene (PP), polytetrafluoroethylene (PTFE), a glass, a silicon, a carbon, a plastic, a rubber, a metal, and mixtures or combinations thereof.

Embodiments of the invention may be employed in any number of other contexts as well. For example, with reference to FIGS. 5-8, biological assay systems and devices typically include a chamber, such as chamber 130, containing one or more capture agents on a chamber surface, such as reaction area 132. Such capture agents are placed in contact with a fluid comprising or including a biological sample suspected of containing macro and small molecules capable of binding to the capture agent(s), which may then be detected using various fluorescence, colormetric, luminescent, radioactive and other labelled as well as label free detection methods known to those skilled in the art.

Assay systems are typically employed in "end-point" assays and, as such, rely on a single introduction of a biological sample to the chamber. The longitudinal assay described in co-pending International Patent Application No. PCT/US10/58112 and U.S. patent application Ser. No. 12/956,117, however, include multiple introductions of a biological sample to an assay chamber. In addition, some embodiments of the longitudinal assay include the introduction of non-biological samples or fluids before, after, and/or between introductions of a biological sample. The non-biological samples or fluids may include, for example, buffer solutions and/or labeling agents.

Figure 9:
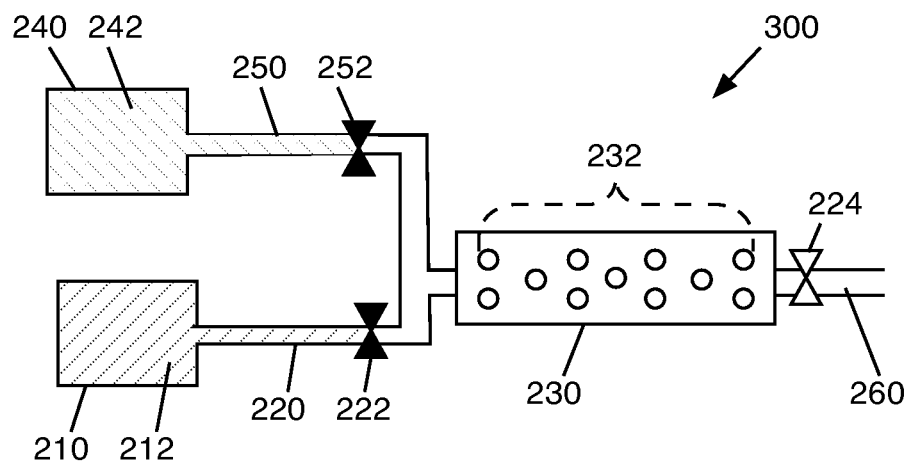
FIGS. 9-16 show schematic views of an assay system according to an embodiment of the invention.

For example, FIGS. 9-16 show schematic views of an assay system 300 and its use in carrying out a longitudinal assay as described in the PCT/US10/58112 and Ser. No. 12/956,117 applications. In FIG. 9, an assay chamber 230 includes a plurality of capture agent spots, collectively referred to as 232 arranged along a surface of assay chamber 230.

Capture agents 232, as well as the analytes to which they bind, may each independently include, for example, proteins, protein fragments, peptides, antibodies (including autoantibodies), antigens (including native antigens), proteins, peptides, aptimers, complexes of antibodies and antigens, complexes of proteins, lipids, cell or tissue lysates and fractions thereof, DNA, RNA, biological agents, chemical agents, biological molecules, chemical molecules and compounds, drug compounds, or molecular or elemental moieties or complexes thereof, which are capable of binding to and forming a complex with a corresponding analyte of interest. As will be apparent to one skilled in the art, various arrangements of capture agent spots 232 other than that shown in FIGS. 9-16 are possible, each of which is within the scope of the various embodiments of the invention.

Figure 10:
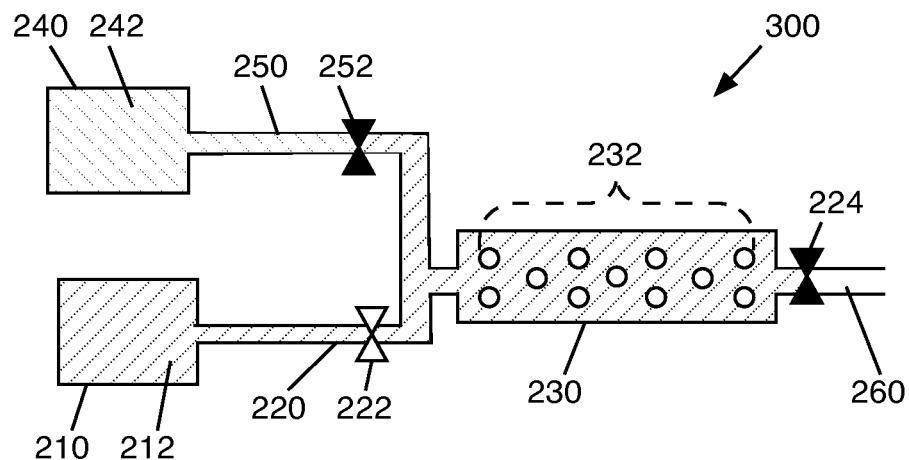
Figure 11:
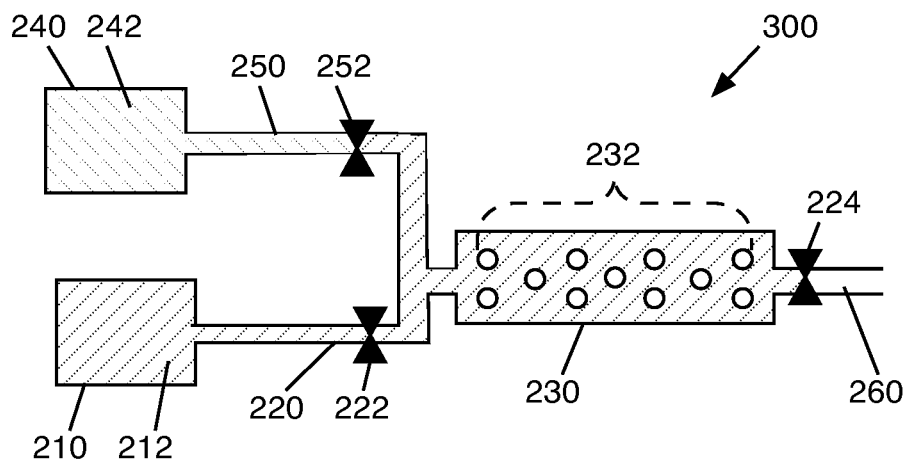

In FIG. 10, assay system 300 is shown in a "fill" state, in which first inlet valve 222 has been opened, releasing first fluid 212 into assay chamber 230, thereby placing first fluid 212 in contact with capture agent spots 232. In FIG. 11, first inlet valve 222 has been closed, trapping a quantity of first fluid 212 within assay chamber 230. Assay system 300 may be held in this state for a period sufficient for target analytes in first fluid 212 to bind with capture agent spots 232. Such a period may be optimized based on the particular binding kinetics of the analyte-capture agent complex to be formed.

As noted above, in some embodiments of the invention, assay chamber 230 may comprise or include one or more flexible material, such that assay chamber 230 takes on a dilated or deformed shape in response to a pressure, such as a static head pressure of first fluid 212, being exerted on an inner surface. In other embodiments, such as those in which first fluid 212 and/or second fluid 242 includes a compressible fluid, such as a gas, assay chamber 230 may comprise or include one or more substantially inflexible or rigid materials, such that assay chamber 230 substantially retains a non-dilated or zero-pressure shape and volume.

Figure 12:
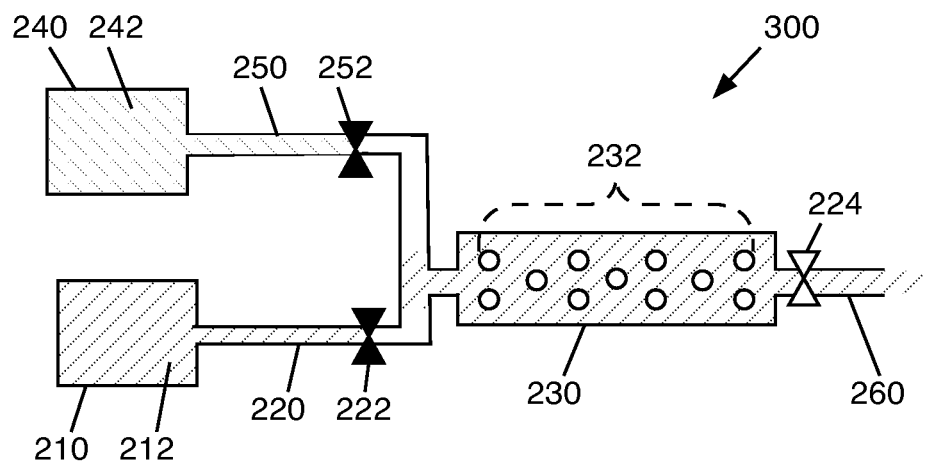

In FIG. 12, assay system 300 is shown in an "empty" state, wherein outlet valve 224 is open and first fluid 212 is discharged from assay chamber 230 through outlet channel 260. In some embodiments of the invention, outlet channel 260 may include or be connected to a pumping device operable to exert a negative pressure on first fluid 212, in which case first fluid 212 may be actively drawn from assay chamber 230.

Figure 13:
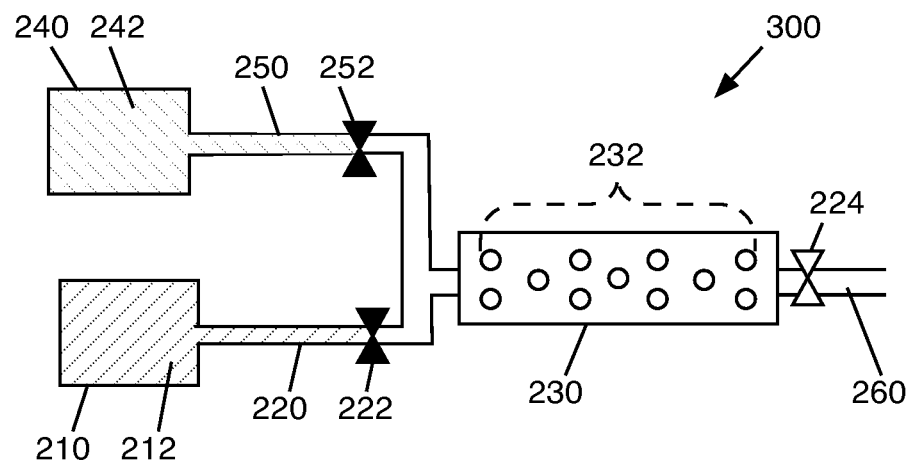
Figure 14:
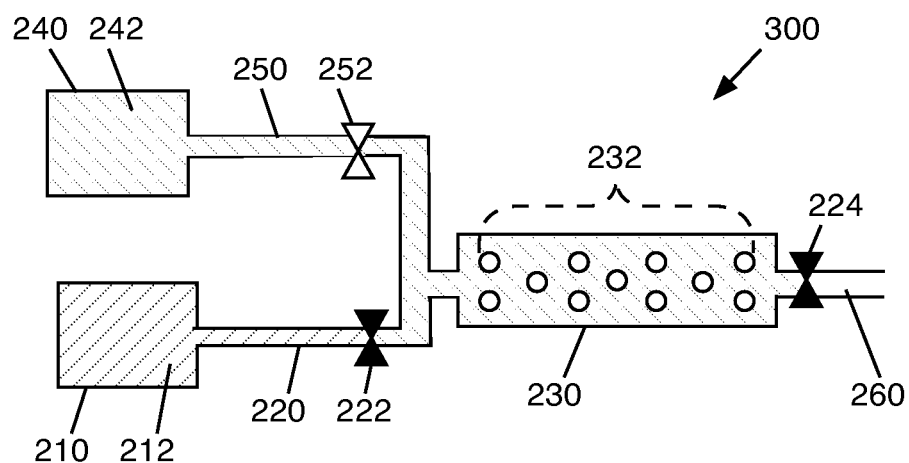

FIG. 13 shows assay system 300 between fluid fills. In FIG. 14, second inlet valve 252 has been opened in a second "fill" state, such that second fluid 242 is placed in contact with capture agent spots 232. As described in the PCT/US10/58112 and Ser. No. 12/956,117 applications, in some embodiments of the longitudinal assay, first fluid 212 may include, for example, an unlabeled analyte and second fluid 242 a label used to detect analytes bound to capture agent spots 232 and/or an analyte-capture agent complex. In other embodiments, first fluid 212 may include a labeled analyte and second fluid 242 may comprise a buffer solution to remove from assay chamber 230 any analyte not complexed with capture agent. In yet other embodiments, first fluid 212 may include an unlabelled analyte and second fluid 242 may comprise a buffer solution to remove from assay chamber 230 any analyte not complexed with capture agent, with detection of any binding carried out using any label free detection method known to those familiar with the art. Other embodiments are possible, of course, and are within the scope of the invention.

Figure 15:
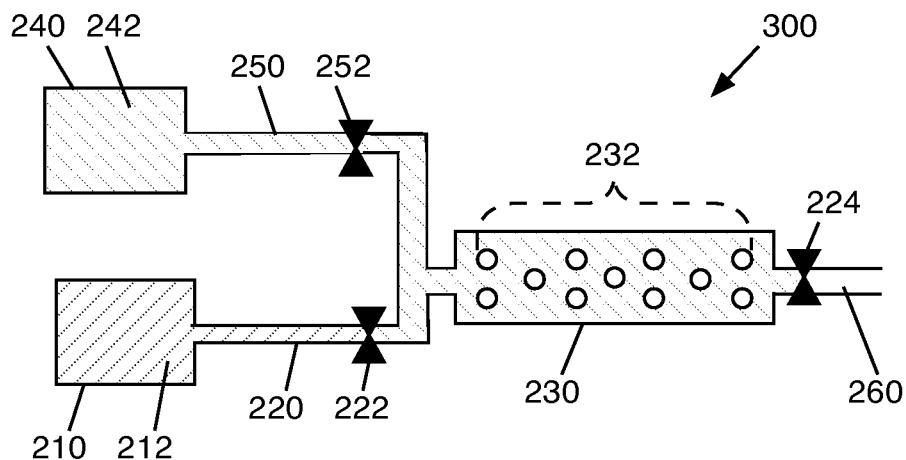
Figure 16:
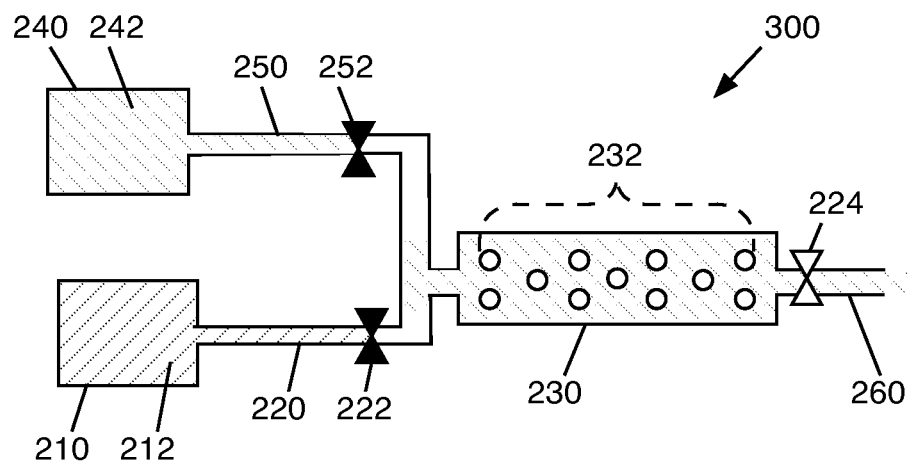

FIG. 15 shows assay system 300 in another "trap" state, in which second inlet valve 252 is closed, trapping a quantity of second fluid 242 within chamber 230. In FIG. 16, a second "empty" state has been entered by opening outlet valve 224 to discharge the quantity of second fluid 242 trapped in FIG. 15.

Figure 17:
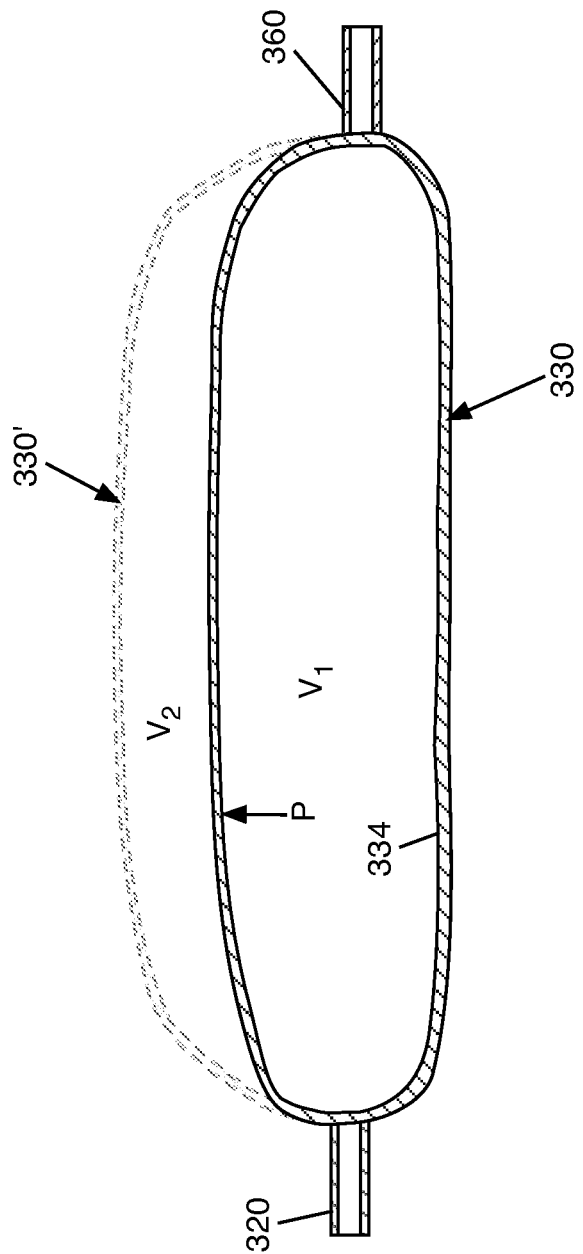
FIG. 17 shows a cross-sectional side view of a dilatable chamber according to an embodiment of the invention.

FIG. 17 show a cross sectional side view of a dilation pump 330 according to an embodiment of the invention. As noted above, dilation pump 330 may include an expandable or deformable material, such as PDMS. As such, an interior surface 334 of dilation pump 330 expands in response to a pressure P exerted against it, such that dilation pump 330 takes on dilation shape 330'. The volume $V_1$ of the undilated dilation pump 330 thereby increases to the greater volume $V_2$ of dilation shape 330'. As shown in FIG. 17, interior surface 334 is shown expanding substantially in one direction, although this is merely for the sake of explanation and simplicity. In other embodiments, interior surface 334 may expand outward in more than one or in all directions.

As noted above, dilation pump 330 is capable of dilation to take on dilation shape 330' under a static head pressure. As such, dilation pump 330 may be employed in any number of applications requiring flow of a fluid, the assays shown and described above in FIGS. 9-16 being merely one possible application.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A pump system comprising:
   a chamber having at least one elastic surface;
   a first inlet valve in communication with and configured to deliver a first fluid to the chamber;
   a second inlet valve in communication with and configured to deliver a second fluid to the chamber;
   an outlet valve in communication with and configured to release either or both of the first or second fluid from the chamber; and
   at least one assay surface within the chamber containing a capture agent for an analyte present in the first fluid and substantially absent from the second fluid,
   wherein the chamber:
      dilates in response to either or both of the first or second fluid exerting a pressure on the at least one elastic surface;
      contains a quantity of either or both of the first or second fluid when so dilated; and
      discharges the quantity of either or both of the first or second fluid through the opened outlet valve.

2. The pump system of claim 1, wherein the pressure includes a static head pressure exerted by a supply of the fluid in communication with either or both of the first inlet valve or the second inlet valve.

3. The pump system of claim 1, wherein the chamber increases in volume in a substantially linear manner in response to a substantially linear increase in the pressure.

4. The pump system of claim 1, wherein the at least one elastic surface includes at least one elastic material.

5. The pump system of claim 1, wherein the chamber has a zero-pressure volume and a dilated volume between about 101% and about 200% of the zero-pressure volume.

6. The pump system of claim 1, wherein the fluid includes a fluid selected from a group consisting of: a liquid, a gas, a supercritical fluid, and mixtures and combinations thereof.

7. The pump system of claim 1, further comprising:
   at least one additional outlet valve;
   at least one additional chamber between and in communication with at least one of the first inlet valve or the second inlet valve and the at least one additional outlet valve, the at least one additional chamber having at least one additional elastic surface,
   wherein the at least one additional chamber:
      dilates in response to either or both of the first or second fluid exerting the pressure on the at least one additional elastic surface;
      contains a second quantity of either or both of the first or second fluid when so dilated; and
      discharges the second quantity of either or both of the first or second fluid through the opened at least one additional outlet valve,
      wherein the second quantity of either or both of the first or second fluid is greater than the first quantity of either or both of the first or second fluid.

8. The pump system of claim 1, further comprising:
   at least one additional outlet valve, wherein the chamber discharges the quantity of fluid through the outlet valve and the at least one additional outlet valve in substantially equal quantities.

9. The pump system of claim 1, wherein the chamber is adapted to receive the fluid through the first inlet valve and the second inlet valve in substantially equal quantities.

10. The pump system of claim 1, wherein the at least one assay surface binds to at least one biological molecule selected from a group consisting of: a protein, a protein fragment, a peptide, an aptamer, an antibody, an auto-antibody, an antigen, a native antigen, a protein complex, a lipid, DNA, and RNA.

11. The pump system of claim 1, further comprising:
   a sensor device for sensing one or more predetermined atoms, ions, molecules, elements, compounds, or compositions in either or both of the first or second fluid.

12. The pump system of claim 1, further comprising:
   a micro reactor including catalyst particles for catalyzing a reaction with either or both of the first or second fluid.

13. The pump system of claim 1, wherein the chamber circulates either or both of the first or second fluid within a circulatory system of a mammal.

14. The pump system of claim 1, further comprising:
   a plurality of flow channels formed as a matrix defining reaction chambers that are arranged in a plurality of fluidic columns and a plurality of fluidic rows,
   wherein the outlet valve is in communication with at least one of the plurality of flow channels, such that the chamber is operable to discharge the quantity of either or both of the first or second fluid into the at least one of the plurality of flow channels.

* * * * *